(12) United States Patent
Goldstein

(10) Patent No.: US 6,819,811 B1
(45) Date of Patent: Nov. 16, 2004

(54) NANO-SIZE GAS SENSOR SYSTEMS

(75) Inventor: Mark K. Goldstein, Del Mar, CA (US)

(73) Assignee: Quantum Group Inc., San Diego, CA (US)

( * ) Notice: Subject to any disclaimer, the term of this patent is extended or adjusted under 35 U.S.C. 154(b) by 133 days.

(21) Appl. No.: 10/010,728

(22) Filed: Nov. 9, 2001

Related U.S. Application Data

(60) Provisional application No. 60/246,988, filed on Nov. 9, 2000.

(51) Int. Cl.$^7$ ................................................ G02B 6/26
(52) U.S. Cl. ......................................... 385/12; 385/32
(58) Field of Search .................... 385/12, 32; 436/134, 436/39; 264/414; 422/57, 82.11; 338/35; 427/372.2; 428/403

(56) References Cited

U.S. PATENT DOCUMENTS

| | | | |
|---|---|---|---|
| 4,043,934 A | | 8/1977 | Shuler et al. ............... 252/186 |
| 5,001,453 A | * | 3/1991 | Ikejiri et al. .................. 338/35 |
| 5,063,164 A | | 11/1991 | Goldstein ................... 436/169 |
| 5,064,693 A | * | 11/1991 | Hayakawa et al. ...... 427/372.2 |
| 5,280,273 A | | 1/1994 | Goldstein ................... 340/632 |
| 5,302,350 A | | 4/1994 | Goswami et al. ............. 422/86 |
| 5,308,771 A | * | 5/1994 | Zhou et al. .................... 436/39 |
| 5,346,671 A | | 9/1994 | Goswami et al. ............. 422/86 |
| 5,405,583 A | | 4/1995 | Goswami et al. ............. 422/86 |
| 5,573,953 A | | 11/1996 | Marnie et al. ............... 436/164 |
| 5,618,493 A | * | 4/1997 | Goldstein et al. ............. 422/57 |
| 5,624,848 A | | 4/1997 | Marnie et al. ............... 436/164 |
| 5,793,295 A | | 8/1998 | Goldstein ................... 340/632 |
| 5,980,831 A | * | 11/1999 | Braiman et al. .......... 422/82.11 |
| 6,207,098 B1 | * | 3/2001 | Nakanishi et al. ........... 264/414 |
| 6,429,019 B1 | * | 8/2002 | Goldstein et al. ........... 436/134 |
| 6,468,657 B1 | * | 10/2002 | Hou et al. ................... 428/403 |

\* cited by examiner

*Primary Examiner*—Ellen E. Kim
(74) *Attorney, Agent, or Firm*—Christie, Parker & Hale, LLP

(57) ABSTRACT

The present invention provides an apparatus and method for determining the presence and/or concentration gases using an optical response. These sensors may be very small, fast and low-cost. The preferred embodiment of the invention is accomplished by means of photon monitoring one or more sensors that respond to the target gas. For example by 1) passing the photons through the sensor, 2) multi-passes of a photon beam through the sensor, 3) by evanescent field absorption (EFA) and 4) by using index of refraction changes to switch the photon from one path to another.

Rapid detection of gases such as CO can be made by multiple passes of photons through a sensor that is absorbing photons of that wavelength range. The photon beam is passed back and forth through the sensor by some means such as using highly reflective optical surfaces or cavity. In essences the multiple internal reflections in a waveguide are similar to the multi-pass photon method except chat the evanescent method only penetrates about 200 nm. The EFA detection system comprises a photon source optically coupled to the sensor and photodiode system, so that the photon flux is a function of at least one other sensor's response to the target gas, e.g., transmits light through the sensor to the photodiode.

In addition, a sensor that changes its index upon exposure to a target gas such CO may be used to switch photons from one waveguide to another proportional to the index changes which is in tern proportional to the concentration of the target gas. Each waveguide may have a different index of refraction and the sensor is in close proximity to both waveguides.

13 Claims, 4 Drawing Sheets

NANO-SIZE GAS SENSOR SYSTEMS

CROSS-REFERENCE TO RELATED APPLICATIONS

This application claims the benefit of U.S. Provisional Application No. 60/246,988.

FIELD OF INVENTION

This invention is in the field of nano-size gas sensors that employ photons to interact with the sensing material in some way. This nano-technology includes the use of photon absorption, refraction, reflection and optical evanescence. The invention incorporates a sensing media, which comprises a chemical complex outside and/or immediately adjacent to a photon source and/or waveguide, e.g., a chemical media that changes its optical properties in response to gases and vapors. There are a number of applications where nano-scale sensors employ evanescent coupling from a waveguide to a porous coating containing a chemical that reacts with a gas or vapor to cause a change in the photon signal through the waveguide. This evanescent method can provide very fast CO response to even low levels of target gases and is also a valuable method to detect a variety of gases that can react with a thin layer coated onto a waveguide. In addition, the nano-scale sensors can be used to employ a multi-pass photon chamber or an optical switch that employs a change to the index of refraction of the sensor to move photons from one waveguide to another. There are other nano-technology sensing methods that can be used to make gas sensor; however, this invention deals with the optical method in the broad sense that photons are used. These optical methods include some interaction of the photons with matter, a photon emitter, a photon detector and a miniature sensor system.

BACKGROUND OF THE INVENTION

In recent years, a number of MEMS and MOEMS devices have been developed. These miniature machines and electro-optical devices may be fabricated using the photolithography techniques developed for silicon devices, such as turbines, switches, sensors and actuators. The macro-machining industry is in its infancy as was the silicon integrated circuit (IC) device industry 40 years ago. As design tools made possible the development of the IC industry, design tools are beginning to give today's researchers the opportunity to design new components combining the physical world needs of sensing and actuators with the rapidly growing capabilities of information technology.

In 1994, Quantum Group proposed to DOE STTR (94-1) the "Evanescent Detection of Gases". This document was proprietary and not a public disclosure, but turned out to be a prescription for a new and better evanescent sensing method, which has been recently reduced to practice. The proposed evanescent system was designed to detect gases such as CO, H2, D2, T2, H2S, $NO_x$, UF6, F2, PuF6, Cl2 and ammonia.

One application of these proposed miniature evanescent sensors is to detect clandestine nuclear or chemical weapon facilities. Other applications are to monitor plumes from existing facilities, measure gases to control engines, fuel cells and other processes, environmental monitoring, safety and detect terrorist activities.

This proposal extends the well-known evanescent fiber optic sensor for detection of various ions in the liquid and gaseous phases (Harrick 1987: Mirabella 1985, Paul 1987; Simhony 1988 and Ruddy et al 1990; S. Shilov et al Proceedings of SPIE Vol. 3918 (2000) and Holmquist 1993). Bell aid Firestone (1986) and others (1985) have stated that many fiber optic systems can convey photon signals with nearly zero attenuation (losses).

Airborne gases and vapors such as hydrocarbons, $NO_x$, hydrogen, carbon monoxide, nerve and mustard agents as well as other gaseous and vapors are generally detected by various instruments in the lab and field. Until very recently, this equipment was very large and expensive. The US government and many companies have embarked on methods to increase the speed of detection and to reduce the size of the detectors. The advent of MEMS and MOEMS has made possible the miniaturization of various sensors. In addition, chemioptical methods developed by Quantum Group in the 1980s have led to commercialization of very low powered biomimetic sensors in the 1990s.

Goldstein et al described examples of a CO sensing using biomimetic sensors, e.g., U.S. Pat. Nos. 5,063,164, 5,618, 493, and patent application Ser. No. 09/487,512 filed Jan. 19, 2000, the contents of which are incorporated by reference. These biomimetic sensors mimic the human response to CO. This chemistry was an improvement of an earlier invention by Shuler and Schrauzer, i.e., U.S. Pat. No. 4,043,934. The Shuler and Schrauzer Patent also teaches the use of a chemistry with high copper ion concentration that converts CO to carbon dioxide even at room temperature, but has limited life and operates over a narrow range of relative humidity.

U.S. Pat. No. 5,063,164 teaches that in the presence of the target gas the danger from hazardous exposures may be determined by monitoring the sensor with a photon source, i.e., passing photons of a specific spectral region through the sensor and monitoring the intensity of the photon beam or using a pulsed photon source to conserve power with a simple photon detector such as a photodiode. There are a number of other target gas sensors that have been disclosed in U.S. Pat. Nos. e.g., Nos. 4,043,934, 5,346,671, 5,405,583, 5,618,493 and 5,302,350, which can detect a target gas such as CO by monitoring the optical properties of the sensor.

Goldstein described several CO detector systems which incorporate these type of optical changing sensors, such as the biomimetic sensor as discussed above, such as U.S. Pat. Nos. 5,280,273, and 5,793,295. Others such as by Marnie et al disclosed a low cost circuit (Apparatus) with software and method for detecting CO in U.S. Pat. Nos. 5,573,953 and 5,624,848. Goldstein et al further disclosed a digital and rapid regenerating means in co-pending patent applications Ser. Nos. 08/026,34 and 60/076,822 herein incorporated by reference. The SIR technology is described in a copending application Ser. No. 60/051,038 filed Jun. 27, 1998, which uses a sensor that responds to CO by a change in its optical properties, for example, as described in U.S. Pat. No. 5,063,164 and the improvement patents mentioned herein in example 1 and co-pending applications.

The gas detector systems include housings that contain one or more photon sources that emit photons in at least a region of the electromagnetic spectrum, a sensor that absorbs photons proportional to the CO exposure, a photo-detector sensitive in the corresponding active region of the spectra, a circuit designed to measure the response, a noise maker or other signal means which are actuated by the circuit and an enclosure. The housing (enclosure) has at least one opening to permit the sound to escape and the CO or other gas to enter. The detector also contains a sensor that may be permanent or may be configured with a battery for convenient replacement or may be mounted within the housing designed for easy replacement and with or without a convenient battery replacement means. Several systems were disclosed in U.S. Pat. No. 5,793,295 by Goldstein issued in Aug. 11, 1998 and is hereby incorporated by reference.

In addition, some preferred embodiments of this invention are portable and can be placed on the vehicles visor or other locations (e.g., pocket, belt, dash) while driving. However, the portable unit is easily removed for use in other location outside the vehicle such as for CO protection in the workplace by workers and/or by contractors, fire person, utility or other serviceperson, etc., or on forklifts and similar vehicles that do not have visors. These types of portable products may be operated on common batteries that can be easily replaced. The sensor system may be replace separately or with the battery. The most accurate detector system able to respond to less than 30 ppm CO contains sensor(s) that need to be replace occasionally (1 to 5 years).

Several low cost sensor systems are disclosed in U.S. Pat Nos. 5,063,164, 5,624,848 (Marnie et al), 5,618,493, (Goldstein et al), 5,280,273 (Goldstein), 5,793,295 (Marnie et at) and higher cost advanced systems are disclosed in co-pending applications Ser. No. 60/076,822 filed Mar. 4, 1998 and a digital CO detector PCT/US97/16846 Filed Sep. 19, 1997, the contents of which are hereby incorporated by reference.

This sensor(s) comprises at least one self-regenerating sensing reagent coated onto a substrate, for example, a high surface area transparent material such as a porous glass. The substrate is made of a solid state material which is sufficiently transmissive or reflective to a specific range of photons in the specific wavelength region of interest to permit detection of optical characteristics of the sensor using an optical source such as a light emitting diode and a photodiode. These optical components and sensor(s) are controlled by a circuit designed to measure the output of the photodiode monitoring the sensor which would alert the passengers through some means and actuate controls as programmed depending on the level of hazard or condition.

These type of detector can be modified to meet any of the following standards: UL 2034 recreational vehicle, British Standard Institute (BSI) for United Kingdom and Japanese standards.

This may be accomplished by one of several software—hardware combinations described in U.S. Pat. Nos. 5,624, 848 and 5,573,953, herein incorporated by reference, known as embodiment I, and co-pending application using digital methodology described in PCT/US97/1686 is known as embodiment 2. Both embodimentS 1 and 2 are preferred embodiments, the first for low cost and the second for performance features and accuracy, i.e., the high-end application.

Most of the current portable digital gas detection products with acceptable accuracy on the market are battery operated and use electrochemical cells for sensors. The units that are accurate are expensive, costing typically $500 to $1000, require frequent calibration and frequent sensor and battery replacements. These electrochemical units can not operate at −40 C. nor can they live for long periods of time at 70 C. Metal Oxide Semiconductor sensors take very large amounts of power and therefore cannot be operated for a reasonable time of 2 years on a small 9 volt battery. The MOS sensors are subject to interfering gases and also lose sensitivity when exposed to silicones often used in the automotive industry. Therefore, there is a need for a low-cost, reliable, low power, accurate, easy to use, and low power consuming unit to detect various gases, such as CO, rapidly even at very low levels as required by fuel cell vehicles. There is a need to incorporate the product into fuel cell vehicles to have a product that can be used to control the reformer with response time of 100 milliseconds.

Furthermore, here is a need for a small CO detector to protect people. A pocket size model has additional advantages of operating over a larger range of humidity and temperature, responding faster and providing more accuracy and more stability than any other technology.

Specifically for the case where the target gas is CO, the sensor is one or more CO optically responding sensors, such as described in U.S. Pat. No. 5,063,164. There are improvements in that technology such as those described in the patent mention above or in copending applications referred to above such as application Ser. No. 60/051,038 filed as an ordinary patent application on Jun. 26, 1998 entitled Air Quality Chamber, herein incorporated by reference. The humidity and air quality system incorporates catalyst formulations sold under the trademark SIR(TM). These sensors are more selective and live much longer than any other sensors on the market.

Acid gases such as sulfur dioxide, sulfur trioxide, oxides of nitrogen, and similar acid compounds may be removed from the air stream by means comprising a porous air filter material impregnated with acid reacting chemical such as sodium bicarbonate, sodium carbonate, calcium carbonate and magnesium hydroxide. In addition, there is a filter section to react with bases such as citric, tartaric, phosphoric, molybdosilicic and other acids impregnated on silica gel or other suitable substrate. A layer of charcoal may separate the acid from the basic layer. A useful air purification system may include four to five active layers separated by inert material such as a porous felt.

An optically responding sensor for detecting the presence of a predetermined target gas, such as carbon monoxide ("CO"), is disclosed in U.S. Pat. No. 5,063,164, the contents of which are hereby incorporated by reference. The sensor comprises at least one self-regenerating sensing reagent coated onto a substrate, for example, a high surface area transparent material. The substrate is made of a solid state material such as silica. The substrate must be sufficiently transmissive to the wavelength of interest to permit detection of optical characteristics of the sensor using an optically coupled light emitting diode and photodiode collectors.

Other methods for detecting gas, such as methane, using evanescent field absorption have been demonstrated using silver halide fiber (Tanaka et al 1985). The halide fibers are very expensive therefore Simhony et al developed a short halide fiber in 1986. Numerous other methods for detecting gases have been developed, such as detection of ammonia using a pH indicator coated in the porous layer (Shahiriari et al. 1988). Saggase et al demonstrated the feasibility of detecting CO, CO2 and methane using AW3 and ZrF3. These methods are expensive and relatively insensitive from 1 to 10 ppm levels. Therefore, a need exists for a more sensitive and faster CO sensor. In addition, there is a need for a sensor that is durable and can operate in fuel cell reformate streams, under high temperature high humidity condition and be durable enough to operate for years without maintenance and calibration. In addition, there is a need for a low cost, easy to manufacture and reproducible CO sensor for fire detection and many other applications, including the detection of CW agents, explosives and other materials.

Therefore, the present invention is important to meet all these necessary requirements; no other technology can meet these requirements.

Certain vehicles such as electric cars powered by fuel cells, were generally expected to comprise a hydrocarbon reformer to convert hydrocarbon to hydrogen, carbon dioxide and carbon monoxide. The CO sensing system may operate off of the main vehicle electric power generated by the fuel cell or other electric generation means and may also have a battery back up system. Increased response speed in the millisecond time frame is a result of the need to control reformers for fuel cells and increase the efficiency of the fuel cell.

SUMMARY OF THE INVENTION

The field of the invention relates to gas monitoring using sensors that respond to gases or vapors by modifying one or more optical property of the sensors.

There are numerous applications for the detection of gases and vapors. One application is to detect hazardous materials such as explosives at checkpoint. Another application is to identify the use of chemical warfare agents. The fuel cell reform requires the detection of CO accurately and reliably at or below 10 ppm. A reference sensor may be used to increase stability and/or to reduce the need for constant calibration. Control sensors measure the difference in the photons passing through the reference and the sensing element. It can compensate for various environmental and other changes.

Example 1 Low power sensing systems. In a preferred low cost embodiment of this invention, e.g., incorporating one or more chemioptical responding sensor(s), a low power consuming sensor monitoring system is used for detecting the presence of a predetermined target gas, such as carbon monoxide ("CO"). Simply by miniaturizing the sensing system, the sensing speed can be increase because these types of sensors change optical properties as the gas diffuses into the pores. These pores are small and therefore it takes time for diffusion to take place. The smaller the sensor, the less time it takes to change the entire sensor or some fraction thereof.

Example 2 illustrates the use of evanescence to increase the sensing speed of an optical sensor. The sensing speed is increase by using the evanescent wave absorption (EFA), because the sensing layer is thin. In one embodiment of the EFA, there is a porous coating that replaces the cladding in a typical waveguide or optical fiber. The key part of the EFA sensor is the coating of the porous cladding. For example, a 125-nm thick coating can be applied to an optical fiber that is 10 microns to 600 nm in diameter. The porous substrate may be made by reaction of the Tetraethyl Orthosilicate (TEOS) with an organic precursor to form an organometallic acid with more than 4 carbons but less than 12 carbons. The reaction is done in a dry box similar to the method for making rare earth metal oxide ceramic precursor composition as described in U.S. Pat. No. 5,662,737, herein incorporated by reference.

In this Example 2 case, one may mix silicon alkoxide with a complexing agent to yield a mixture of complexing agent/alkoxide of silicon. The mixture is then hydrolyzed and the precursor composition is isolated and is stable in air. The solubility of the precursor can be tailored to dissolve in various solvents and be controlling the structure and functional groups. The at least partial dissolution in a solvent creates pre-ceramic liquid that can be used to coat the waveguide. Pore size can be controlled by the amount of solvent and pore agent used. The pore agent can be a polymer of a sub-micron insoluble material or a combination of the above. The pore agent may preferably consist of a material that is interconnected such that when it is burned out the pore structure is uniform and interconnected. A mixture is of cyclodextrins (CDs) and polymers with functional groups that self-assemble with the CDs. In some cases, the organic complexing agent may act as the pore agent by itself or with another additive. The coating may be applied by dip coating, spraying or other similar method.

The fiber is placed in a chamber with an optical emitter and sensor. The photons are placed into the waveguide at one end and read at the other. The EFA is measure at time zero and at various exposure of a target gas such as CO. The coiling of the fiber reduces the size of the chamber and increases the sensitivity of the sensing system by increasing the evanescent wave outside the core fiber into the outer cladding.

For the case where the target gas is CO, a circuit is designed to measure the EFA output of the photodiode and/or its rate of change, dI/dt. Under certain condition, the derivative is proportional to the carbon monoxide (CO) concentration, $[CO]=k_1\{dI/dt\}$, at other times
$[CO]=k2\{I(n)\}$
when dI/dt is very near zero And, when dI/dt is not linear such that the second derivative is not very near zero, than a weighted average is calculated, and the constants $k_3$ and $k_4$ represent the proportion of each component on the weighted average which may be determine empirically. After the constants have been determined for each type of sensor, then the CO concentration can be approximated by the following equation $$[CO]=c\{k_3[dI/dt]+k_4[I(n)]\}$$

The approximation can be employed easily and can limit the cost of the digital alarm or detector.

In the case where the gas to be measured is a fuel cell reformate stream, the CO in the stream reacts with one sensor in the linear range. There are two sensors as described in an earlier U.S. patent application Ser. No. 09/487,512 filed Jan. 19, 2000. One embodiment of the invention comprises a control system, which consists of two sensors and a valve system to allow the control of air and reformate alternately, such that one sensor is always measuring the CO and perhaps the information can be used for controlling other systems. This embodiment is referred to as K CO Detection system hereafter. The control sensor measures CO in the hydrogen stream effectively and at least one sensor is being regenerated by the air stream. The two or more sensors are monitored photometrically, one in the hydrogen stream and at least one in the air.

In the use of porous silica coatings on a core optical fiber and then coating or self-assembling a gas sensing material on the porous surface, there is a well-known alkoxide coating method that was developed by Jeff Brinker at Sandia, which was first tried; however, the coating pore structure was only about 1 to 3 nm in diameter. This process is good for some sensor material. The CO sensor requires a pore size of 20 to 25 nm (200 to 250 Angstroms). This pore structure, disclosed in a previous patent for a CO sensor, U.S. Pat. No. 5,618,493 issued August 1997, exceeds 15 nm or 150 Angstroms. If the average pore diameter is larger than 350 m, the transparency in the 500 nm to 1000 nm wavelength range drops off sharply.

Therefore, the ideal range for CO detection over a normal range of RH is between 15 nm to 30 nm for use with visible and near IR wavelength photon emitters and detectors. A patent by R. Shoup discloses a method to make pore structure of the appropriate size using potassium silicate and colloidal silica. This method can be used by itself or combineed with the other method mentioned above.

Once the coating is in place, any number of coatings can be added to the porous silica to sense a target gas. The sensitivity depends on the evanescent wave, which is outside the core fiber and enters the porous clad sensor.

Paul et al 1987 showed that the evanescent power of an evanescent field absorption (EFA) fiber optic sensor has a well defined electric field distribution outside the fiber waveguide, which decays exponentially as it moves radially from the outer surface. This evanescent field is typically 0.01 to 0.1 percent, except in single mode fibers, which can be as high a 0.1 to 1.0 percent or even higher.

The eigenvalues for the solution of the equation for a photon in a waveguide can be employed to compute the normalized frequency as follows:

$$V^2 = U^2 + W^2$$

Where U and W are eigenvalues for the core and cladding that arise from the solutions in an electric field in an optical fiber (Snyder 1974). For a porous sensor clad optical fiber, V may be defined as $$V = 2\pi r/\lambda \{\sqrt{[n(f)^2 - n(c)^2]}\}$$

where r is the fiber radius, and n(f) and (c) are the indices of refraction of the fiber and porous cladding, respectively. Thus the equation demonstrates that for small values of V, i.e., small diameter sensors and for porous coatings with different indices of refraction from the fiber, there will be an evanescent absorption in the sensing media when it is exposed to the target gas, assuming the appropriate wavelength photons are employed. Therefore, Micro-Optical Electronic Machine Systems (MOEMS) are an excellent way to manufacture these sensors. The method involves the use of photolithography, etching, coating, etc., as described in "Silicon Micromechanics: Sensors and Actuators on a Chip" by Roger Howe et al IEEE Spectrum, July 1990; "Mirrors on a Chip" by Jack Moore, IEEE Spectrum, November 1993; V. Kieman, Laser Focus World March 1997 pp 63–64; and Steven Ohr, Electronic Engineering Times, Aug. 4, 1997 pp. 1–146, as well as DAPRA DOD Website under MTO, MEMS and MOEMS.

The changes in photon intensity dI at the end of the fiber is proportional to the length I of the sensing region, the evanescent field absorption, i.e., proportional to the radius of the fiber, the fibers optical and physical properties and the sensitivity of the sensing layer S as well as the concentration of the target gas such as (CO). Thus the concentration of the (CO) can be monitored by measuring the rate of change of the evanescent absorption with respect to time t.

$$d(\text{evanescent absorption})/dt = k(CO)$$

For other gases, the k may be different and for some sensing media, the equation may vary depending on material properties.

In some cases, such as CO, k is a constant. In general, K may be some function that needs to be determined experimentally. In the CO case, the concentration of CO is proportional to the change in the photon intensity of the specific wavelength over a dt interval. This is true in the initial response; however, the nature of one such CO sensor coating has been shown to be proportional to both I and dt/dt.

Under certain condition, the derivative of the transmitted photons with respect to a time interval plus the actual transmitted photon intensity is proportional to the carbon monoxide (CO) concentration, $$[CO] = k_1\{dI/dt\} + I(K_2) \text{ at other times}$$

$$[CO] = k_2\{I(n)\}$$

when dI/dt is very near zero

And, when dI/dt is not linear such that the second derivative is not very near zero, than the sum of the two, i.e., I(n) and dI/dt is divided by 2 or is averaged or a mean. In addition, a weighted average is feasible such as represented by the general equation:

$$[CO] c\{k_1[dI/dt] + k_2[I(n)]\}$$

The approximation can be employed easily and can limit the cost of detector and has the capability of digital display.

Other approximations are also possible, e.g., the sum of averages or weighted averages over a series of registers $$[CO] = k_1(dI/dt) + K_2[I(n)]$$

This method may be useful in producing digital displaced CO concentrations.

The fiber optic system has limitation in size; however, optical waveguides can be miniaturized using Micro Optical Electro Machining (MOEMS). The optical system may be useful for a variety of applications from sensing to controlling aircraft.

Example 3 illustrates the use of index refraction change to direct the photons. If the sensor is used as an optical switch, then photons in one waveguide may be directed to a second waveguide. There may be a photon emitter that places photons (of a specific wavelength range) within waveguide 1. Assuming there is no reaction from the target gas, then these photons stay in waveguide 1; however, if the target gas exceeds a predetermined level, the index of refraction changes such that the photons are directed to the waveguide 2.

Example 4 illustrates the use of a system that passes photons through the sensing area more than once. This method is referred to a multi-pass because the photons are passed through the active area many times. The method is well known in spectroscopy for detecting gases. In this case, we are using the thin layer of a porous solid and amplifying the absorption by using reflectors or some other means to direct the photons through the thin reacted sensor media more than once. The more time the greater the absorption and thus the greater the change in the signal.

One of the key advantages of the above examples is the increased speed of response over conventional system described earlier. The fast sensors such as CO devices may be incorporated into vehicles, which can respond to CO or other gases in a number of ways to protect occupants, control fuel cell reformers, and control air quality. The technology may be generally applied to the detection of chemical warfare (CW) agents as well as other gases. For example, hazards such as hydrogen, hydrocarbons, CO, ammonia and various toxic pollutants may be monitored in near real time with very short delay of the order of millisecond. In addition, some of these methods can be miniaturized with low cost.

There are provided several preferred embodiments of the present invention. These embodiments include both apparatae and methods for determining the concentration of various target gases at very fast speed for which examples were given above.

1. Miniaturize conventional absorption: Small sensors are as limited by diffusion rate.
2. Thin layer multi-pass: This invention uses photons that pass through the sensor many times, either using a multi-pass through the porous sensor.
3. EFA: Sensor comprises a waveguide coated with a porous sensing media.
4. Index of refraction changes: One such method uses the sensor to switch photons from one area to another.

The present invention relates to a sensing system, which comprises one or more optical responding sensors, which comprise a coating onto porous transparent substrate. This field of invention relates to a sensor and a sensing apparatus incorporating at least one photon emitter such as an LED or laser diode and a photodetector such as a photodiode. Standard photon multiplexing techniques used in the telecommunication optical fiber industry are useful for identifying some agents;others require multiple photon emitter. These preferred embodiments use very little power and have long life.

These multi-pass and EFA sensors are fail safe. These sensors operate over the range from minus 40 C. to +70 C. The technologies are Solid State and use either infrared or visible or both.

Coiling an optical fiber makes one embodiment of an evanescent wave sensor. One preferred embodiment of the EFA method is for sensing CO. The EFA sensing system consists of at least two separate materials: one, an optical waveguide and the other, a porous coating which incorporates a material that changes its optical properties when exposed to one or more target gases, and a means to pass one or more wavelength photons through the fiber such that one or more photon wavelengths are absorbed due evanescent coupling. The specific pattern recognition from the differences in absorption of various wavelengths yields a spectral signature that is capable of rapid and specific identification of most compounds of interest. For many simple compounds, only one or two wavelengths may be needed. In addition, the use of multiple wavelength can identify several compounds at one time. The porous layer is made very thin, about 100 nm to 200 nm (1000 to 2000 angstroms). It is then coated with a sensing medal that changes its optical properties when exposed to CO. The coating may be applied directly. By -measuring the evanescent absorption changes as a function of time and/or the absolute light intensity value, the concentration of CO and other gases may be determined.

For applications in controlling fuel cell reformers, two sensors may be required. In a reformate stream comprising hydrogen and very little oxygen, two sensors may be used, one in the reformate stream and the other in clean air. When monitoring the optical response I (nl) of the sensor (S1) at a time t, this optical response is proportional to the CO concentration within the one chamber. The other chamber has a similar design and therefore will also have a similar sensor, which will be regenerating while the other is responding.

This EFA embodiment relates to an evanescent field absorption sensor with a waveguide and an adjacent sensing media EFA-SM to accurately detect CO over a wide range such as 5 to 1000 or even 10 to 15000 ppm over a short time, such as 1000 milliseconds. This basic EFA-SM concept may be used to detect hazardous gases, such as CO. These devices may be incorporated in or attached to various vehicles and may be portable units such that it can be easily carried for applications in locations other than the vehicles or from one vehicle to the other. This invention includes applications comprising gas detector systems, such as a carbon monoxide (CO) sensor to very rapidly detect the presence of CO for reformer controls. In addition, a signaling means may be incorporated to alert the people of fire, CO hazard or other gaseous materials. Optionally, the novel device can display digital information on the target gas, e.g. concentration, compute and/or display the Time Weighted Average (TWA), peak concentration over some predetermined time interval, total dose from target gas exposure, concentration, etc., and then display the information on the vehicle dash or other location.

The EFA can be computed by subtracting the background loss.

The K series sensors contain a much higher concentration of copper ions than a biomimetic composition disclosed in U.S. Pat No. 5,063,164, herein incorporated by reference. The concentration of copper is more than 1000 times that of the photometric (color) change sensors. This is because these sensors are responding to IR absorption in the near IR below the threshold. The reference sensor response to humidity is nearly identical to the humidity response of CO sensor. The threshold of the high copper CO sensors may be 200 ppm or 20,000 ppm.

BRIEF DESCRIPTION OF THE DRAWINGS

The invention will be better understood with reference to the following detailed description and accompanying drawings wherein.

DETAILED DESCRIPTION OF THE FIGURES

Figure 1:
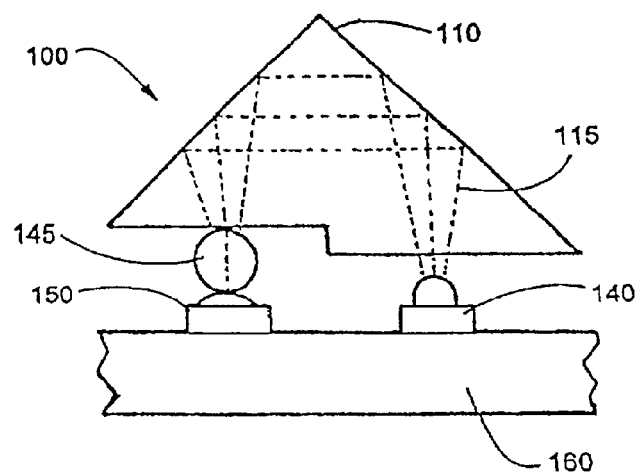
FIGS. 1 and 1a are a miniaturized CO sensor using surface mount LED and Photodiode (PD) and prism to direct the photon through the sensor and then to the PD.
Figure 1A:
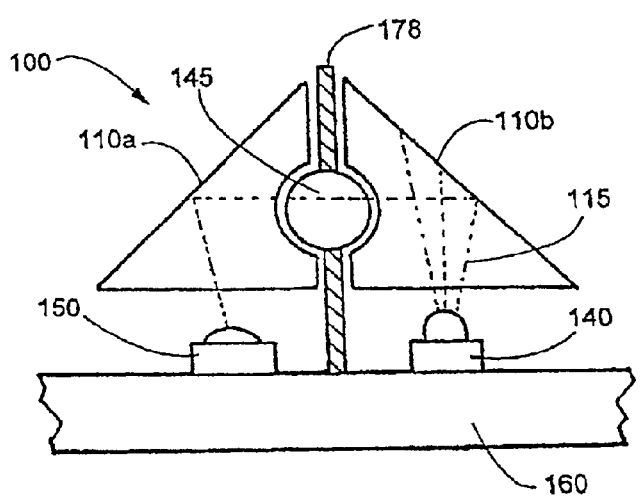

FIGS. 1 and 1a illustrate a miniature surface mount LED 140 and photodiode 150 in an optical sensing system 100. The prism 110 directs photons 115 to a sensor 145. The photons 115 from the LED 140 pass through a target gas, which react with the target gas or vapor. There are two basic optical techniques that are incorporated as embodiments of this fast optical monitoring method, i.e., 1) transmission and 2) reflection. The prism waveguide 110 may be replaced with other waveguide shapes (not shown). In FIG. 1, the prism transmits and then reflects photons 115, which pass through the miniaturized sensor 145 and then strike the photodiode 150. In FIG. 1a, prism surface 110b trnasmits the photons 115 which pass through the miniaturized sensor 145 and are then reflected by prism surface 110a before striking the photodiode 150.

Figure 2:
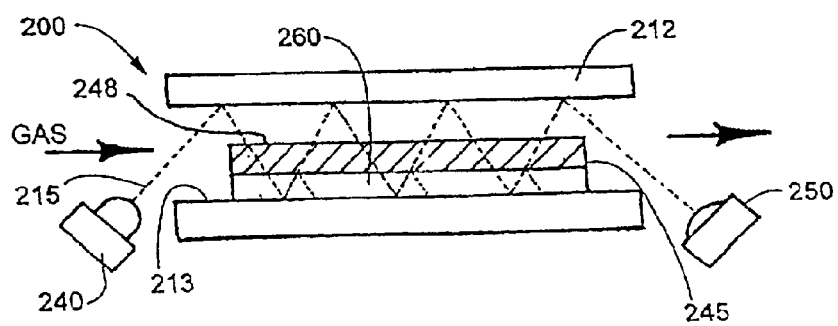
FIG. 2 is a typical thin coating sensor that utilizes a multi-pass photon arrangement.

FIG. 2 illustrates a multi-pass transmissive sensing apparatus 200. This sensing device 200 can be used for a variety of gases. For purpose of an example, the use of CO as the target gas will be described; however, it in no way is limiting the target gases of this method. Passing photons 215 through a sensor 245 many times as shown in FIG. 2 may enhance the transmission method if reflectors 212 and 213 are very reflective such that the signal is preserved. FIG. 2 illustrates a multi-pass photon device 200 that comprises the sensor 245 that comprises a porous optical material, which is coated with a sensing agent (not shown) to form the sensor 245. The target gas is directed to a sensing surface 248, which reacts with the surface layer 248 in time t(1) to a depth d(1). The photons 215 emitted from a photon source 240 are reflected back and forth through the sensor 245 by the reflectors 212 and 213. The photons are absorbed in the portion of the coating that reacts with the gas in time t and the signal is read by monitoring a photodetector 250. Ten reflections through the sensing material (245) may be provided in this embodiment.

Figure 3:
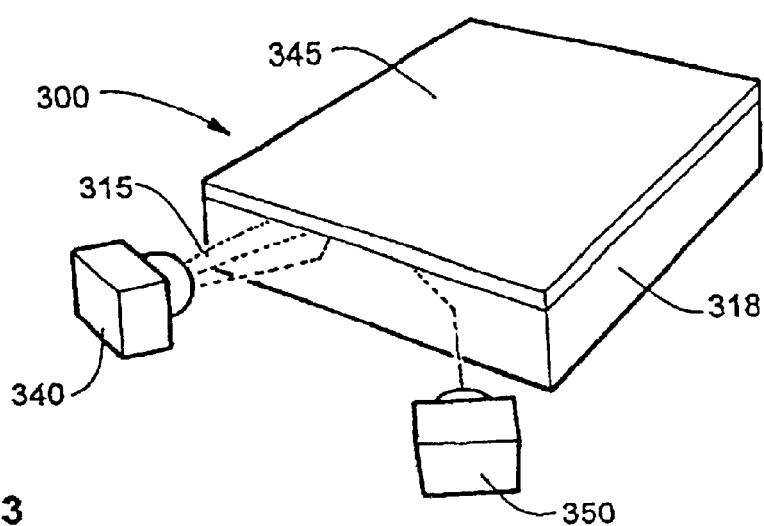
FIG. 3 illustrates an evanescent sensing device to measure the optical change on a very small surface at a depth d, which was coated on a waveguide.

FIG. 3 illustrates an EFA sensing apparatus 300. In the case where the target gas is CO, a porous sensor coated may consist of a porous transparent material about 1000–2000 angstrom (100 to 200 nm) thick coated with about 1 to 2 molecular layers of a supramolecular chemistry, which is optically responsive to CO. The sensing material comprises a chemical reagent comprising at least one of the following groups:

Group I Palladium salts selected from the group consisting of palladium sulfate, chloride, and bromide.

Group 2 Heteropolymolybdates such as silicomolybdic acid, ammonium molybdate, alkali metal molybdates.

Group 3 Copper salts of sulfate, chloride, bromide and perchlorate.

Group 4 Alpha, beta gamma or delta cyclodextrins and their hydroymethy, ethyl and propyl derivatives.

Group 5 Soluble salts of alkaline and alkali chlorides and bromides and mixture thereof;

Group 6 Organic solvent and/or co-solvent and trifluorinated organic anion selected from the group including dimethyl sulfoxide (DMSO), tetrahydrofuran (THF), dimethyl formamide (DMF), trichloroacetic acid, trifluoroacetate, a soluble metal trifluroacetylacetonate selected from cation consisting of copper, calcium, magnesium, sodium, potassium, lithium, or mixture thereof; and Group 7 Soluble inorganic acids such as hydrochloric acid, sulfuric acid, sulfurous acid, nitric acid, and strong oxidizers such as peroxide, or mixture thereof.

To form a sensing layer 345, which is located just outside a waveguide 318, comprises the process of fabricating the EFA sensing device comprising the steps of coating the waveguide with a porous silica layer between 20 nm and 200 nm, and then coating the porous silica surface with a sensing agent.

A method of producing the porous transparent layer which provides the sensing platform for a self-assembled supramolecular sensing agent in an evanescent field absorption (EFA) sensor, is made by starting with a silicon alkoxide, and further comprising the step of reacting the silicon alkoxide with an organic material with carbons from 4 to 12, and further involves the hydrolysis of the complex to form an organo-silicon compound that is a stable compound and is soluble in non-polar solvents, and further dissolving the solid organo-silicon in the solvent and then coating the waveguide with the solution and further drying the coating and then heating it to drive off the solvent. The waveguide substrate such as silicon dioxide substrate and the porous silica are next slowly heated to 500 to 900 C. and then cooled slowly to room temperature. This cooling may be accomplished simply by shutting off the oven and leaving the oven to cool over night.

The size of the pores is important and must be keep at 10 to 30 nm, with the preferred embodiment at about 200 to 270 nm. The preferred embodiment may be fabricated using the information disclosed in US Patents as well as the method disclosed in the US Patent Applications given above. In addition, the method may comprise the steps of adding a pore forming agent to the solvent containing the organo-silicon, and then dip or spin coating the waveguide, drying and heating to remove all solvent and to burn out the pore forming agent that results in a 150 to 300 nm pore structure.

The CO sensor generally regenerates in air if the air has no or very small amount of CO. In the absence of CO, i.e., operating in clean air, the sensor is in the normal state or condition indicated by a transmission of light (photons in the wavelength band of interest), which is indicated by a characteristic optical value I(0) and a zero value. If a target gas such as CO is present, the sensor equilibrium is shifted as the reagent undergoes changes in its optical density, i.e., the sensor begins to change its photon (optical) interaction properties on the surface. The gas interacts with the outer surface fast, but is then limited by diffusion through the small pore. A typical monolith sensor darkens or lightens on its outer surface closest to the source (gas) depending on the particular type of CO sensor. After a time t(0)+t(1), which depends upon the gas (such as CO) concentration and the duration of exposure to CO, the sensor has changed over a thickness D(1). If it were practical to measure the D (1) absorption only by aligning a photon emitter 340 with a photodetector 350 as shown in FIG. 3, then a rapid measurement could be made. In practice, it is difficult to make this measurement because of alignment issues, therefore a multi-pass sensing system is very useful to provide a very fast and accurate response.

Figure 4:
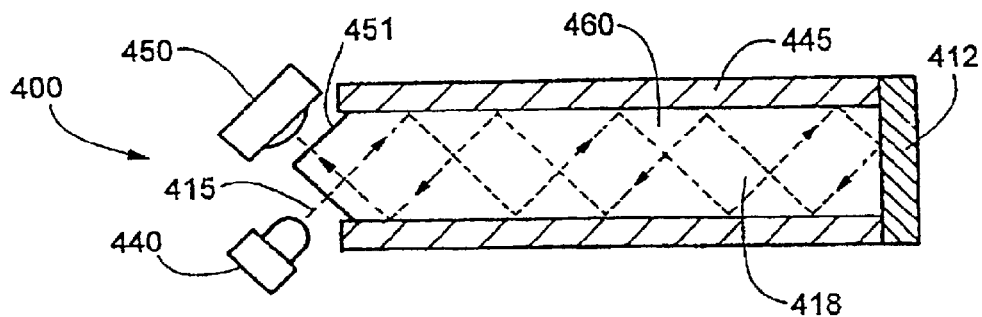
FIG. 4 illustrates an EFA sensing device with a straight waveguide with a coating that interacts with a target gas.

FIG. 4 illustrates a straight waveguide system 400 with porous coatings 445 on at least two sides and a reflector 412 on the side opposite a photon entry side 451. An LED 440 emits photons 415 of a particular wavelength, e.g., 400 nm to 1100 nm. The photons 415 enter a waveguide 418 through the polished surface 451 with the beam of photons 415 entering perpendicularly to the surface. The photons exit perpendicularly onto a photodiode 450 as shown. The coatings 445 sense the target gas such as CO with evanescent interaction in the outer cladding 445. The invention employs the use of internally reflected photons to monitor the gas exposure and concentration of the target gas in the cladding (coating on a waveguide). This EFA device 400 is illustrated in FIG. 4, which illustrates a possible MEMS optical waveguide 418.

Figure 5:
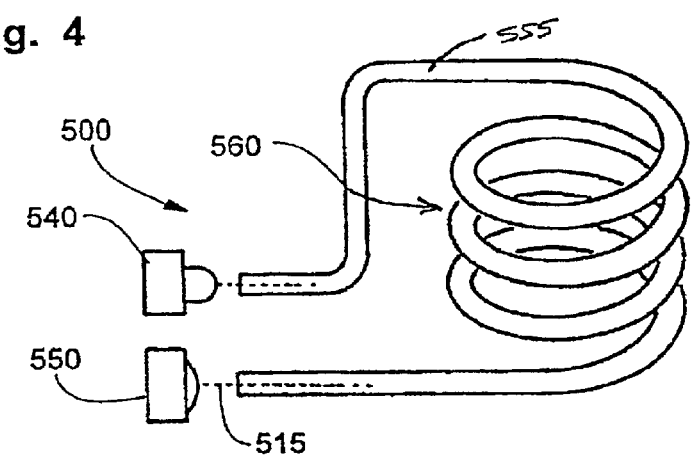
FIG. 5 illustrates an EFA sensor that comprises a coiled optical fiber core with a porous coating that reacts to the target gas.

FIG. 5 illustrates a fiber optic coil used as an evanescent ring system 500 for the detection of gases and vapors. The EFA ring system 500 can also be configured to operate using an optical coil 560 with sensing media (not shown) coated onto at least a portion of the coil 560, which is located close to an optical fiber 555. The evanescent coupling using porous coating on coiled fibers has been proposed earlier by Goldstein and Holmquist and others as mentioned above. The novel aspect of these gas sensors is that a porous transparent cladding is first prepared, coated at 100 to 2000 angstroms and processed at high temperature over 350 C. Then, a sensing material is applied using self-assembly nano-technology with molecules that comprise a mixture.

The step of coating the waveguide is to immerse the waveguide in a chemical reagent comprising at least the following groups for a period of time:

Group 1 Palladium salts selected from the group consisting of palladium sulfate, chloride, bromide and mixture thereof;

Group 2 Heteropolymolybdates such as silicomolybdic acid, ammonium molybdate, alkali metal molybdates;

Group 3 Copper salts of sulfate, chloride, bromide and mixtures thereof;

Group 4 Alpha, beta, gamma, and or delta cyclodextrins and their derivatives and mixtures thereof;

Group 5 Soluble salts of alkaline and alkali chlorides and bromides and mixture thereof;

Group 6 Inorganic or organic acid and or salt of organic or inorganic compound that dissolve in the mixture in the presence of the acid(s); and Group 7 Strong oxidizer such as nitric acid, hydrogen peroxide or mixture thereof;

and further removing the waveguide and porous outer layer from the solution and then drying the waveguide system slowly over I hour to 7 days to form the supramolecular sensing complex. Next, the waveguide system is heated to about 50 C. to 80 C. for a period of time varying between a few hours and a few days depending on the size of the oven the circulation of the oven and the amount of sensor in the oven.

Figure 6:
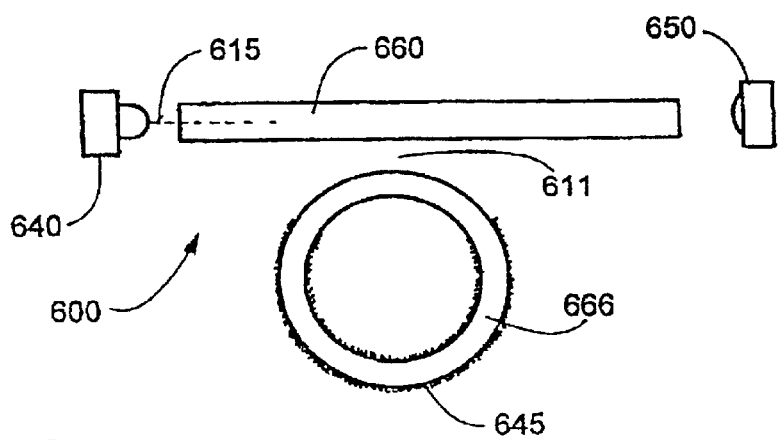
FIG. 6 illustrates an EFA-ring sensing device that provides a time measurement of the
signal decay from the ring back to the waveguide.

FIG. 6 illustrates an EFA sensing devices 600 that can be fabricated using MOEMS technology. This device contains an evanescent coupling that can move photons 615 from a waveguide 660 to a ring 666 and back. While the photons are traveling in the ring, the EFA takes place proportional to the concentration of the target gas such as CO. A photon emitter 640 pulses an amount of photons, of which a portion is coupled into the ring 666 because of the close spacing and the materials used. The photons move from the emitter 640 to the waveguide 660, to the ring 666, and then a portion is coupled back to the straight waveguide 660 after each circumference passage of the photons around the ring 666. Some of these photons 615 are absorbed by sensing coating 645, which absorption is proportional to the concentration of the target gas (not shown). FIG. 6 shows the evanescent system 600 that is positioned such that a portion of these photons is coupled in either direction. If the decay time of the signal measures similar to plasma resonance, then a low cost fast responding sensing system is accomplished.

Figure 7A:
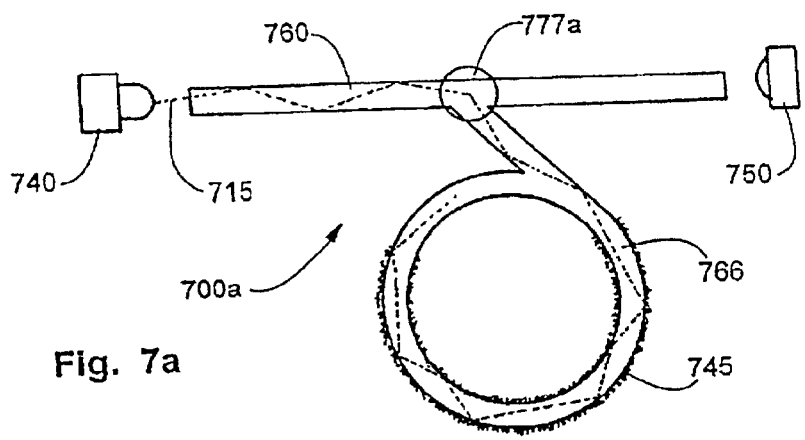
FIGS. 7a and 7b illustrate switchable electro-optical devices, which move the photons from the straight waveguide to the ring EFA sensor, which absorbs photon proportional to the concentration of target gas, and then switch the photons back to the waveguide where they are measured.
Figure 7B:
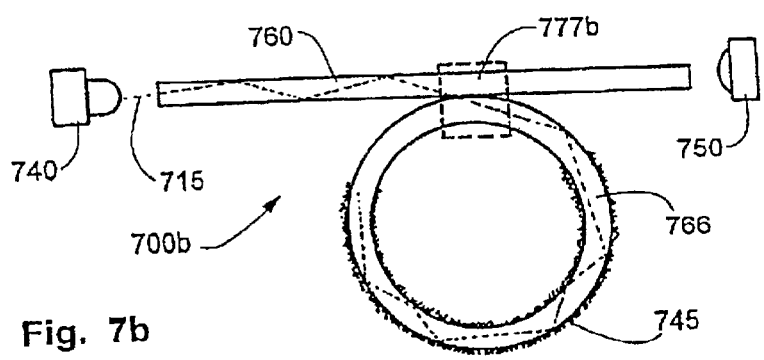

FIGS. 7A and 7B illustrate the use of a means to switch photons into a ring coated with sensing media 745. Photons 715 are passed from a waveguide 760 through a switch 777a or 777b to a ring 766. Then, the position of the switch may be changed to allow the reduced photon signal to be transferred back to the waveguide 760. The photons 715 go around and around the ring 766 and are evanescently coupled to the sensing material 745 proportional to the thickness of the coating, the diameter of the ring, the material and the index of refraction, as well as the gas concentration of the target gas. As they go around the small ring 766, the photons spend a portion of their time outside the ring waveguide in the sensing cladding 745. If the target gas has reacted with the cladding media 745, then some of the photons will be EFA in that cladding proportional to the concentration of the target gas (not shown). The longer the photons spend time in the small ring 766, the more that is absorbed. In a few microsecond or a few milliseconds, the switch can be activated allowing a portion of the photons 715 to be passed back to the straight waveguide 760 and a photodiode 750 can be place at one or more end(s). The photon signal is then read by the photodetector 750. The difference between the intensity of photons measured at some interval of time t(I) is a measure of the target gas concentration in near real time, that is, less than 1 second and perhaps less than 1 millisecond depending on the parameters discussed above, gas concentration and the speed of the switch.

Several methods of forming transparent porous sensor substrates are given below. The major steps in forming a uniform porous coating, which are bonded to a waveguide, are given for silicon dioxide but can be used for many other metal oxides. Examples 7-1 through 7-3 have porous silica of controlled pore sizes with the average pore diameter 200 to 270 nm as measure by a Quantachrome BET Model XXX. It is preferred that the pore diameter not vary more than plus or minus 15%. FIG. 7 illustrates four steps to manufacture a sensor for evanescent field absorption.

Step 1: The precursor is prepared. In Example 7-1 and 7-2, the precursors are TEOS and TMOS, respectively. In example 7-3, it is a silicon tetra 2-ethylhexanoic acid. Other organo-silicon compounds are feasible and the few examples given are not intended to limit the method.

Step 2: Involves preparing the solution and applying the coating by dip or spray.

Step 3: Age, dry and then heat to about 500 to 675 C.

Step 4: Impregnate or coat the porous silica with a sensing material and process.

EXAMPLE 7-1

Water is mixed with nitric acid to form a 0.01N acid. Next, 0.75 grams of polyacrylic acid (Aldrich 19205-5) mw 250,000 is blended with 10 ml of 0.01N acid to obtain a clear solution. Add 10 ml of TEOS; stir gently, then heat in a closed container to 60 C. for 10 minutes. Next, dip a waveguide into the solution. The solution is useful for about 1 hour.

After coating, dry the coated waveguide in air for 1 hour then wash with nano-pure water and ethanol. Then, dry at 60 C. for 1 hour. The dried sample has a pore size of 25 nm. The thickness of the coating can be controlled by the time of immersion. During the first few minutes of gelling, the coating is 50 to 75 nm thick. At 10 to 30 minutes, the coatings are about 80 to 120 nm, and the coatings done after 30 minutes are larger than 120 nm.

EXAMPLE 7-2

0.023 grams Polyvinyl pyrrolidone (Aldrich 85656-8 mw 40,000) is dissolved in 10 ml of nano-pure water. Add 5 ml of TMOS and stir gently. Heat the solution at 55 C. in closed container for several minutes, then open and place one test fiber into the mixture for a few seconds and remove. Test the coating for smooth bonding, size and uniformity. As soon as the proper coating is obtained, dip coat as many waveguide as possible within ten minutes. Then age for 2 hours each of the dipped waveguides. Then wash 3 times with water and ethanol. The pore average size will be about 25 nm.

EXAMPLE 7-3

One preferred embodiment uses 2-ethylhexanoic acid. The evaporation of the solvent such as cyclohexane forms the green ceramic, which after controlled firing forms a thin porous silica layer with average pore diameter of 20 to 25 nm (200 to 250 Angstroms).

The ratio of the 2-ethylhexanoic acid added to the total silicon alkoxide is preferably in the range between I to I to 2.7 to I on a molar basis. The green ceramic is heated slowly to about 500 C. to 600 C. The heating cycle can take from 12 to 24 hours depending on the amount of materials use in the furnace and the thickness of the coating.

EXAMPLE 7-4

Any examples above are feasible; however, for clarity, the preferred manufacturing method is shown. A coating solution preparation: approximate 50 grams of above silicon tetra 2-ethylhexanoic acid is added to 250 grams of cyclohexane to form a clear liquid. The liquid is sprayed through a standard air/liquid spray gun onto an unclad optical fiber. It instantly forms an adherent coating under standard lab conditions. The fiber is then heated to 550 C. in 12 hours and then allowed to cool to room temperature. The oven is opened and the coated fiber removed. The fiber is then placed in a humidity chamber for 24 hours, after which it is placed in a solution containing the supramolecular complex described in U.S. Pat. Nos. 5,063,164 and 5,618,493. It is feasible to machine thousands of these devices in a single chip using MEMS technology as referenced above.

Figure 8:
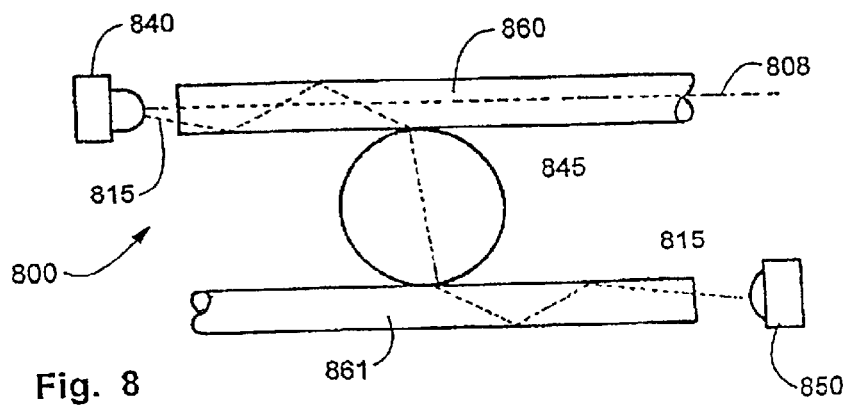
FIG. 8 illustrates the use of a gas sensor used to switch the photons from one waveguide to another by means of an index of refraction change. The photons move through the sensing element to the parallel waveguide on the opposite side of the sensor.

FIG. 8 illustrates an index sensing switch system 800 comprising a photon source such as an LED 840 and a waveguide 860 to receive photons 815 from the photon source, a portion of which is captured by the acceptance angle and stays in the waveguide (WG1) 860 by total internal reflection. The WG1 860 is optically coupled to sensor 845 and is also optically coupled to waveguide WG2 861, which is located on the opposite side of the sensor from the waveguide 860. There is a photodiode 850 located at the far end of WG2 861. If the photons 815 transfer from WG1 to WG2 by a change in the optical properties of the sensor 845, then the photodiode 850 will register the change proportional to the amount of photons striking the photodiode 850. If the gas such as CO (not shown) is what changes the optical properties to cause the photons to switch from the waveguide 860 to the waveguide 861, then the system can sense this change very rapidly in the order of milliseconds. The smaller the system is, the more quickly the sensor changes. FIG. 8 illustrates the use of a sensing switch system 800 that uses the change in index of refraction due to the reaction of sensor chemistry with a target gas or vapor. As the index changes, the photons move from one position to another position (not shown).

EXAMPLE 8-1

An example is of an index of refraction change to switch the photons from waveguide (WG) 1 to waveguide (WG) 2 through the sensor S (the sensor may be a K sensor for fuel cell applications).

One skilled in the art would appreciate an apparatus and method for tracking the response of optically responding sensors for a variety of target gases such as CO. Today, current low-cost digital CO products cannot operate reliably for years with common batteries, such as 1.5 volt AA, AAA or 9 volts or similar batteries. Such an apparatus and method would increase the desirability of a wide variety of products from home detectors to military monitors, medical products, breath diagnostics to industrial controls to automotive gas sensing products and fuel cell reformers. Many of the current digital CO products on the market are battery operated. These CO digital detectors use electrochemical cells for sensors. They are very expensive, require frequent calibration, and frequent replacement. Or, they use Metal Oxide Semiconductor (MOS) sensors which take very large amounts of power and therefore cannot be operated for a reasonable time of years or even months on small batteries such as a 9 volt battery. Therefore, there is a need for a reliable, low-cost accurate digital CO detector.

Furthermore, there is a need for small, fast responding detectors to detect chemicals that may be released in a battlefield or civilian environment by an adversary. The tiny sensor can be fabricated on a small chip only a few microns. Therefore, it can stand the g forces needed to send these sensors into the battlefield in small vehicles or shells. The novel invention provides all of these advantages and has additional advantages of operating over a larger range of humidity and temperature, responding faster and providing more accuracy and more stability than any other technology.

One skilled in the art may appreciate a low powered gas (such as CO) sensing apparatus, which can also, measure and display gas concentration by calculations from the response of EFA for a variety of target gases.

Such an apparatus and method would increase the desirability of a wide variety of products from home detectors to military, medical products, breath diagnostics to industrial controls to automotive gas sensing products. These target materials include $NO_x$, CO, Hydrocen, $CO2$ as well as chemical warfare agents and explosive vapors and many other volatile molecules.

What is claimed is:

1. A method for determining the presence and concentration of gases by means of monitoring the change in photons in a sensing system comprising passing photons through a waveguide, which is coated with a porous transparent material and impregnated with a sensing media, and further comprising means to couple the optical signal in the waveguide to the sensing material in the coating via evanescent wave absorption, and further comprising a display means, and further comprising at least one sensor which responds to at least one target gas and can be monitored by an electronic circuit and further comprising a photon emitter and a photon detector, and further comprising coating the waveguide with a porous silica layer between 20 nm and 200 nm and then coating the porous silica surface with a sensing agent.

2. The method as claimed in claim 1 wherein the step of coating the waveguide is to immerse the waveguide in a chemical reagent comprising at least one of the following groups for several hours:

Group 1: Palladium salts selected from the group consisting of palladium sulfate, chloride, bromide and mixture thereof;

Group 2: Heteropolymolybdates such as silicomolybdic acid, ammonium molybdate, alkali metal molybdates;

Group 3: Copper salts of sulfate, chloride, bromide and mixtures thereof;

Group 4: Alpha, beta, gamma, and or delta cyclodextrins and their derivatives and mixtures thereof;

Group 5: Soluble salts of alkaline and alkali chlorides and bromides and mixture thereof;

Group 6: Inorganic or organic acid and or salt of organic or inorganic compound that dissolve in the mixture in the presence of the acid(s); and Group 7: Strong oxidizer such as nitric acid, hydrogen peroxide or mixture thereof and further removing the waveguide and porous outer layer from the solution and then dry the waveguide system slowly over 1 to 2 days to form the supramolecular sensing complex.

3. An apparatus that measures the identity and concentration of gases and vapors comprising at least one optical evanescent field absorption sensor; and further comprising a photon emitter and a photon detector; and further comprising a waveguide coated with a porous transparent material that is an oxide; and further comprising a ring waveguide coated with a sensing material coated onto the transparent porous oxide, the sensing material changing its optical properties when exposed to a target gas; and further comprising means to couple photons from the straight waveguide section to the ring waveguide and remove a portion of those photons and then detect a target gas by monitoring the amount of photons at the end of the straight waveguide.

4. An apparatus that measures the identity and concentration of gases and vapors comprising at least one optical evanescent field absorption sensor; and further comprising a photon emitter and a photon detector; and further comprising a waveguide coated with a porous transparent material, the waveguide in the shape of a ring and further comprising a very thin coating on the ring with a sensing material in the coating; and further comprising a straight waveguide in the immediate vicinity and running tangent to the ring waveguide and means to switch the photons from the straight waveguide to the ring waveguide and a means to switch the photon from the ring back to the straight waveguide and means to detect the change in evanescent field absorption due to one or more target gases by monitoring the amount of photons at the end of the straight waveguide.

5. An apparatus of claim 4 comprising more than one light source each with different wavelengths and means to read each wavelength independently.

6. An apparatus of claim 5 further comprising several photon sources of different wavelengths and at least one photon detector and means to measure each wavelength separately by pulsing the photon source at different times and reading the many different wavelengths; and further an analog to digital converter to convert the analog signal to digital and further comprising means to store the digitized signal from each wavelength and compare the signal patterns from each wavelength to a pattern stored in the microprocessor and an algorithm that will interpret the various signal patterns to identify the gases present and estimate their concentrations.

7. An apparatus that measures the identity and concentration of gases and vapors comprising at least one optical evanescent field absorption sensor; and further comprising a photon emitter and a photon detector; and further comprising a waveguide coated with a porous transparent material that is an oxide; and further comprising a sensing material coated onto the transparent porous oxide that changes its optical properties when exposed to a target gas, and further comprising comprising at least two sensors and sensor monitoring system and means to condition the sample and means to switch the gas from the reformate stream to a air stream and back periodically; and further comprising a microprocessor to control the switching and to process and digitize the signals from the photodetector(s) to determine the CO gas concentration in a fuel cell reformate stream, and further comprising means to incorporate the device into a fuel cell vehicle to control the reformer process by measuring CO in milliseconds; and further comprises a sensor to selectively detect CO in hydrogen and CO2, means indicate need of service, and means to protect the occupants from the gases detected.

8. An evanescent photon absorption sensor based gas detector apparatus of claim 7 further comprising:
at least two photon sources in each sensing chamber;
at least one photodetector optically coupled to receive photons from the photon sources as modified by the sensor and at least two photon source for emitting photons at different wavelengths that in term measure the response of the sensor(s) to CO and humidity; and a means to determine the CO and humidity component to the signal; and
further comprising a chemical reagent comprising at least one of the following groups for several hours:
Group 1: Palladium salts selected from the group consisting of palladium sulfate, chloride, bromide and mixture thereof;
Group 2: Heteropolymolybdates such as silicomolybdic acid, ammonium molybdate, alkali metal molybdates;
Group 3: Copper salts of sulfate, chloride, bromide and mixtures thereof;
Group 4: Alpha, beta, gamma, and or delta cyclodextrins and their derivatives and mixtures thereof;
Group 5: Soluble salts of alkaline and alkali chlorides and bromides and mixture thereof; and
Group 6: Inorganic or organic acid and or salt of organic or inorganic compound that dissolve in the mixture in the presence of the acid(s).

9. An apparatus as claimed in 8 comprising means to sense at least two sensors in a differential measuring system comprising:
a photon sources and detector means to sense the target gas;
control means for sensing environment parameters that affect the target gases and compensate for those changes;
means for measuring the difference in the characteristics of the sensor; and
means for determining magnitude of the measured difference in photon characteristics and the intensity of the difference, including means to monitor accurately the target gas concentration under a wide range of temperature and humidity.

10. An apparatus of claim 7 further comprising a circuit that is used to calculate the CO concentration and further means to display the digital value of the CO concentration, further comprising means to measure and compensate for temperature value; and further comprising a sensor which consists of a porous silica materials coated with a chemical reagent comprising at least one of the following groups:
Group 1: Palladium salts selected from the group consisting of palladium salts of sulfate, palladium sulfite, palladium pyrosulfite, palladium chloride, palladium bromide, palladium iodide, palladium perchlorate, $CaPdCl_4$, $CaPdBr_4$, $Na_2PdCl_4$, $Na_2PdBr_4$, $K_2PdCl_4$, $K_2PdBr_4$, $Na_2PdBr_4$, $CaPdCl_xBr_y$, $K_2PdBr_xCl_y$, $Na_2PdBr_xCl_y$ (where x can be 1 to 3 if y is 4 or visa versa), and organometallic palladium compounds such as palladium acetamide tetrafluroborate and other similarly weakly bound ligands, and mixtures of any portion or all of the above;

Group 2: Molybdenum, vanadium, and/or tungsten salts or acid salts selected from the group consisting of silicomolybdic acid, phosphomolybdic acids, and their soluble salts, molybdenum trioxide, ammonium molybdate, alkali metal, or alkaline earth metal salts of the molybdate anions, mixed heteropolymolybdates, or heteropolytungstenates and mixtures of any portion or all of the above;

Group 3: Soluble salts of copper halides, sulfates, nitrates, perchlorate, and mixtures thereof, copper organometallic compounds that regenerate the palladium such as copper tetrafluoroacetic acid, copper tritlouroacetylacetonate, and other similar copper compound, and copper vanadium compounds such as copper vanadate, and soluble vanadium compounds that can be incorporated into the group 2 molybdenum based-keg ions such as phosphomolybdic acid and silicomolybdic acid, and mixtures of any portion or all of the above;

Group 4: Supramolecular complexing molecules selected from the cyclodextrin family including alpha, beta, and gamma as well as their soluble derivatives such as hydroymethyl, hydroxyethyl, and hydoxypropyl beta cyclodextrin, crown ethers and their derivative, and mixtures of any portion or all of the above;

Group 5: Soluble salts of alkaline and alkali halides, and certain transitional metal halides such as manganese, cadmium, cobalt, chromium, nickel, zinc, and other soluble halide such as aluminum; and any mixture thereof;

Group 6: Organic solvent and/or co-solvent and trifluorinated organic anion selected from the group including dimethyl sulfoxide (DMSO), tetrahydrofuran (THF), dimethyl formamide (DMF), trichloroacetic acid, trifluoroacetate, a soluble metal trilluroacetylacetonate selected from cation consisting of copper, calcium, magnesium, sodium, potassium, lithium, or mixture thereof; and Group 7: Soluble inorganic acids such as hydrochloric acid, sulfuric acid, sulfurous acid, nitric acid, and strong oxidizers such as peroxide, or mixture thereof.

11. An apparatus of claim 7 wherein the microprocessor comprises means for assigning sensor reading values to each of the measured photon characteristics;

means for determining differences between sensor reading values;

memory for storing the differences;

an alarm register for adding the sum of a plurality of the differences stored in the memory; and means for entering an alarm mode when value of the alarm register exceeds an alarm point and;

means to signal when the change has occurred above a predetermined level.

12. An apparatus that measures the identity and concentration of gases and vapors comprising at least one optical evanescent field absorption sensor; and further comprising a photon emitter and a photon detector; and further comprising a waveguide coated with a porous transparent material that is an oxide and further comprising a sensing material coated onto the transparent porous oxide that changes its optical properties when exposed to a target gas, and further comprising two sensors in two separate housing each comprising more than one photon source each of a different wavelength; and further comprising a sample conditioning system that consists of a thermoelectric cooling section and a heating section, between the cold section and the heating section is a membrane to prevent water from passing and means to periodically remove excess water; and further comprising at least two separate chambers with valves connecting the sensors alternately to the air and a reformate gas sample; further comprising a display means to indicate the need to perform maintenance; and further comprising at least two sensor, which one responds to the CO in the hydrogen stream while at least one remains outside the stream and is regenerated in clean air, and further comprising means to switch the flows of clear air through one of the sensor chambers and a portion of the hydrogen stream through another sensor chamber and a control means to assure that the concentration of CO directed to the fuel cell is less than a predetermined concentration; and further comprising at least two optically responding sensors, which response to the CO and humidity; and can be monitored by a low-powered electronic circuit with a current draw of less than 25 microamps; and further comprising a supramolecular complex that is self assembled on to a semi-transparent silica porous substrate; and further comprising a thin semi-transparent sensing layer on the porous transparent substrate comprising palladium, copper and calcium metals ions, halogen anions and cyclodextrins and there derivatives and an acid.

13. A method of producing a porous transparent layer which provides a sensing platform for a sensing agent in an evanescent field absorption sensor, comprising starting with a silicon alkoxide; and further comprising reacting the silicon alkoxide with an organic material with carbons from 4 to 12; and further comprising hydrolyzing the complex to an Organo-silicon compound that is stable and soluble in a non-polar solvent and further dissolving the solid Organo-silicon in the solvent to form a solution and then coating a waveguide with the solution and further drying the coating and then heating it to drive off the solvent, and further comprising a process using at least one optically responding sensor(s) monitored by two different photon sources and a photodetector and the system is calibrated to initiate a signal at a predetermined level of target gas for a predetermined period of time, the method comprising the steps of: intermittently measuring the optical (transmission) characteristics of the sensor(s); and further comprising means to monitor a reformate stream by sampling the stream alternately as a means to alternately direct a sample of gas to the first sensor and air to the second sensor and to reverse the process to allow the first sensor to regenerate and further comprising a sample condition means so that sample of reformate and air enter the sensing chambers at a predetermined relative humidity, pressure and temperature.

* * * * *

UNITED STATES PATENT AND TRADEMARK OFFICE
CERTIFICATE OF CORRECTION

PATENT NO.     : 6,819,811 B1
DATED          : November 16, 2004
INVENTOR(S)    : Goldstein It is certified that error appears in the above-identified patent and that said Letters Patent is hereby corrected as shown below:

Title page,
Item [57], ABSTRACT,
Line 2, after "concentration", insert -- of --.
Line 17, delete "essences", insert -- essence --.
Line 18, delete "chat", insert -- that --.
Line 27, after "such", insert -- as --.
Line 29, delete "tern", insert -- turn --.

Column 16,
Lines 59 and 67, delete "mixture", insert -- mixtures --.
Line 64, delete "and or", insert -- and/or --.

Column 17,
Line 1, delete "and or", insert -- and/or --.
Line 2, delete "compound", insert -- compounds --.
Line 5, delete "mixture", insert -- mixtures --.
Line 34, delete "photon", insert -- photons --.
Line 62, delete "comprising comprising", insert -- comprising --.
Line 64, delete "a air", insert -- an air --.

Column 18,
Line 5, delete "means indicate", insert -- means to indicate --.
Line 13, delete "source", insert -- sources --.
Line 14, delete "term", insert -- turn --.
Lines 22 and 31, delete "mixture", insert -- mixtures --.
Lines 28 and 32, delete "and or", insert -- and/or --.
Line 33, "compound", insert -- compounds --.
Line 35, before "8", insert -- claim --.
Line 38, delete "sources", insert -- source --.
Line 55, delete "materials", insert -- material --.
Line 63, delete "visa", insert -- vice --.

Column 19,
Line 13, delete "tritlouroacetylacetonate", insert -- trifluoroacetylacetonate --.
Line 14, delete "compound", insert -- compounds --.
Lines 16-17, delete "molybdenum base-keg", insert -- molybdenum-based key --.
Line 24, delete "derivative", insert -- derivatives --.
Line 29, delete "delete "halide", insert -- halides --.
Line 35, delete "trilluroacetylacetonate", insert -- trifluoroacetylacetonate --.
Line 36, delete "cation", insert -- cations --.
Line 41, delete "mixture", insert -- mixtures --.

UNITED STATES PATENT AND TRADEMARK OFFICE
CERTIFICATE OF CORRECTION

PATENT NO. : 6,819,811 B1
DATED : November 16, 2004
INVENTOR(S) : Goldstein

It is certified that error appears in the above-identified patent and that said Letters Patent is hereby corrected as shown below:

Column 20,
Line 3, delete "housing", insert -- housings --.
Line 15, delete "sensor", insert -- sensors --.
Line 24, delete "response", insert -- responds --.
Line 33, delete "metals", insert -- metal --.
Line 33, delete "there", insert -- their --.
Lines 41 and 42, delete "Organo-silicon", insert -- organo-silicon --.

Signed and Sealed this

Twenty-seventh Day of December, 2005

JON W. DUDAS
*Director of the United States Patent and Trademark Office*